US008702957B2

(12) United States Patent
Wang et al.

(10) Patent No.: US 8,702,957 B2
(45) Date of Patent: Apr. 22, 2014

(54) ELECTROCHEMICAL DETECTION OF SILICA SPECIES

(75) Inventors: Joseph Wang, San Diego, CA (US); Aristotelis Dimitrakopoulos, Saint Martin de Nigelles (FR); Celine Le Ninivin, Verneuil sur Seine (FR); Stephane Mabic, Rouvres (FR)

(73) Assignees: Arizona Board of Regents for and on behalf of Arizona State University, Scottsdale, AZ (US); EMD Millipore Corporation, Billerica, MA (US)

( * ) Notice: Subject to any disclaimer, the term of this patent is extended or adjusted under 35 U.S.C. 154(b) by 396 days.

(21) Appl. No.: 12/666,492

(22) PCT Filed: Jun. 29, 2007

(86) PCT No.: PCT/US2007/072585
§ 371 (c)(1),
(2), (4) Date: Jan. 7, 2010

(87) PCT Pub. No.: WO2009/005522
PCT Pub. Date: Jan. 8, 2009

(65) Prior Publication Data
US 2010/0193377 A1    Aug. 5, 2010

(51) Int. Cl.
*G01N 27/26* (2006.01)
*G01N 33/20* (2006.01)

(52) U.S. Cl.
USPC ........ 205/775; 205/794.5; 204/406; 204/409; 436/72; 436/73; 435/287.1; 422/68.1; 422/82.01

(58) Field of Classification Search
USPC .............. 204/410, 411, 421–435, 406, 409; 205/775, 794.5; 422/68.1, 82.01; 435/287.1; 436/73, 72
See application file for complete search history.

(56) References Cited

U.S. PATENT DOCUMENTS

| 3,403,081 | A | 9/1968 | Rohrback et al. |
| 4,145,255 | A | 3/1979 | Schiller et al. |
| 4,651,325 | A | 3/1987 | Wang et al. |
| 4,686,681 | A | 8/1987 | Paranto et al. |
| 4,715,710 | A | 12/1987 | Andersen |
| 4,865,992 | A | 9/1989 | Hach et al. |
| 5,131,999 | A | 7/1992 | Gunasingham |

(Continued)

FOREIGN PATENT DOCUMENTS

| CN | 101021503 A | 8/2007 |
| DE | 2927615 | * 1/1981 |

(Continued)

OTHER PUBLICATIONS

Neil et al., Electroanalyais 1997, 9, No. 17.*

(Continued)

*Primary Examiner* — Jennifer Dieterle
(74) *Attorney, Agent, or Firm* — Fish & Richardson P.C.

(57) ABSTRACT

A systems and apparatus for measuring non-electroactive materials in liquids using electrochemical detection. A first electrical activity of a electroactive material is detected in absence of a target non-electroactive material (Step 120). A second electrical activity of the electroactive material is detected in presence of the target non-electroactive material (Step 130). A difference between the first and second electrical activities is obtained, and based on the obtained difference, a concentration of the target non-electroactive material is identified (Step 140).

19 Claims, 8 Drawing Sheets

(56) References Cited

U.S. PATENT DOCUMENTS

| | | | |
|---|---|---|---|
| 5,192,416 | A | 3/1993 | Wang et al. |
| 5,292,423 | A * | 3/1994 | Wang ........................... 204/434 |
| 5,676,820 | A | 10/1997 | Wang et al. |
| 5,733,786 | A | 3/1998 | Green |
| 5,942,103 | A | 8/1999 | Wang et al. |
| 6,063,259 | A | 5/2000 | Wang et al. |
| 6,409,909 | B1 | 6/2002 | Spichiger-Keller et al. |
| 6,468,785 | B1 | 10/2002 | Wang et al. |
| 6,514,762 | B1 | 2/2003 | Wang |
| 6,682,647 | B1 | 1/2004 | Wang |
| 6,790,341 | B1 | 9/2004 | Saban et al. |
| 6,793,889 | B2 | 9/2004 | Naatz et al. |
| 6,873,762 | B1 | 3/2005 | Wang et al. |
| 6,878,255 | B1 | 4/2005 | Wang et al. |
| 6,893,552 | B1 | 5/2005 | Wang et al. |
| 7,176,036 | B2 | 2/2007 | Wang et al. |
| 7,355,706 | B2 | 4/2008 | Girvin et al. |
| 7,381,564 | B2 | 6/2008 | Matschenko et al. |
| 2003/0201191 | A1 * | 10/2003 | Kovarsky et al. ............. 205/775 |
| 2005/0008860 | A1 | 1/2005 | Garnier |
| 2009/0026076 | A1 | 1/2009 | Yang |
| 2010/0193377 | A1 | 8/2010 | Wang et al. |

FOREIGN PATENT DOCUMENTS

| | | | |
|---|---|---|---|
| GB | 2240630 | * | 1/1991 |
| JP | 5508703 | A | 12/1993 |
| JP | 2005513423 | A | 5/2005 |
| WO | WO9111720 | A1 | 8/1991 |
| WO | WO2005121792 | A1 | 12/2005 |
| WO | WO 2009/005522 | | 1/2009 |
| WO | WO 2009/123645 | | 10/2009 |

OTHER PUBLICATIONS

Xu et al. (Analytical Chemistry, 66 Mar. 1994).*
Fogg et al. (Analyst, Dec. 1983, vol. 108, pp. 1485-1489).*
Machine translation of DE 2927615.*
Marczenco et al. (Analytical Spectroscopy, 2001).*
Wang et al. (Electroanalysis, Jan. 18, 2006, No. 1, 59-63).*
International Search Report and Written Opinion dated Sep. 16, 2008 for PCT Application No. PCT/US07/72585, 13 pages.
"Series 5000 Silica Analyzer" Hach Company http://www.hach.com/hc/search.product.details.invoker/PackagingCode=6000000/NewLinkLabel=Series+5000+Silica+Analyzer, 1 page, 2009 [accessed Dec. 22, 2009].
Hungarian Authorized Officer Tamas TAKACS, Written Opinion dated Nov. 12, 2010 for Singapore Patent Application No. 200908665-3, 6 pages.
Notice of Reasons for Rejection for Japanese Patent Application No. 2010-514732, dated Feb. 2, 2012, 6 pages (full English translation).
Singapore Application No. 201007270-0, Written Opinion dated Sep. 12, 2011, 9 pages.
Series 5000 Silica Analyzer Data Sheet, Hach Company, 2007, 4 pages.
PCT/US2008/059467, International Search Report and Written Opinion, mailed Oct. 21, 2008, 10 pages.
Shemirani, Farzaneh et al., "Simultaneous Determination of Traces of Cadmium and Zinc by Adsorptive Stripping Voltammetry", Canadian Journal of Analytical Sciences and Spectroscopy, 2005, vol. 50, No. 4, pp. 175-181.
Duwensee, Heiko et al., "Adsorptive stripping voltammetric detection of daunomycin at mercury and bismuth alloy electrodes", International Journal of Electrochemical Science, 2007, vol. 12, pp. 498-507.
EcloxTM Water Test Kit Trademark Specimen dated Feb. 2004 and Nov. 2004, filed with the USPTO Nov. 2004, 7 pages.
Hibbert et al., Anal. Chem., 62 (1990), pp. 1015-1019.
Sequeira et al., Electroanalysis, 11 (1999), pp. 494-498.
K. Mazuranic et al., Spectrophotometric determination of Si(IV) with 3,6-dichloro-2,5-dihydroxy-1,4-benzoquinone, Microchemical Journal 1992, vol. 46, No. 3, pp. 374-378.
J. F. van Staden et al., "Simultaneous determination of copper, lead, cadmium and zinc using differential pulse anodic stripping voltammetry in a flow system" Analytica Chimica Acta, 2000, vol. 411, Issues 1-2, pp. 201-207.
Neil G. Carpenter et al.,"Microelectrode Procedures for the Determination of Silicate and Phosphate in Waters—Fundamental Studies" Electroanalysis, vol. 9, No. 17, pp. 1311-1317, 1997.
Hach DR 5000™ UV-VIS Spectrophotometer and DR 2800™ Portable Spectrophotometer, Mar. 17, 2007, 3 pages.
Hach DR 2800 Portable Spectrophotometer, Aug. 27, 2006, 1 page.
Manfred Paeschke et al. "Voltammetric Multichannel Measurements Using Silicon Fabricated Microelectrode Arrays" Electroanalysis, 1996, vol. 8, No. 10, pp. 891-898.
J. F. van Staden et al., "Determination of copper by anodic stripping voltammetry on a glassy carbon electrode using a continuous flow system" Fresenius J Anal Chem, 1997, vol. 357, pp. 624-628.

* cited by examiner

ELECTROCHEMICAL DETECTION OF SILICA SPECIES

CROSS REFERENCE TO RELATED APPLICATIONS

This application is a national stage application of and claims priority under 35 U.S.C. 120 from International Application No. PCT/US2007/072585, filed Jun. 29, 2007, and entitled "Electrochemical Detection of Silica Species". The disclosure of the prior application is considered part of (and is incorporated by reference in) the disclosure of this application.

TECHNICAL FIELD

This application relates to electrochemical detection.

BACKGROUND

Detection of silica in a liquid (e.g., water) can use colorimetric techniques. For example, a silica-molybdate complex can be formed and measured by measuring absorption of probe light at a wavelength of 450 nm. Alternatively, a silica-molybdate-heteropoly blue complex can be formed and measured by measuring absorption of probe light at a wavelength of 810 nm. These and other colorimetric processes may require the addition of several chemical reagents in various steps with each step taking up a defined period of time to allow for sufficient mixing and reaction.

SUMMARY

This application describes, among others, techniques, systems and apparatus related to detecting inorganic species (e.g., silica) in water using electrochemical processes.

In one aspect, detecting a metal complex includes applying a voltage to a buffering solution that includes the metal complex and is free or inorganic species to be detected. A first current associated with the metal complex is measured in absence of the inorganic species. Inorganic species are added into the buffering solution, and a second current associated with the metal complex in the presence of the added inorganic species is also measured. A difference between the first current and the second current is obtained to identify a concentration of the added inorganic species in the buffering solution.

Implementations can optionally include one or more of the following. Measuring the first and second currents can further include applying an accumulation potential followed by a scanning potential. Applying the accumulation potential can include applying an accumulation potential of an amplitude that includes 0.5 volts. The accumulation potential applied can also be applied for a period of time that includes 60 seconds. Also, applying the scanning potential can include applying a scanning potential having at least one from a group that includes an amplitude of 25 millivolt, a step potential of 4 millivolt, and a frequency of 25 hertz. Further, applying a voltage can include applying a voltage to a buffering solution that includes a metal complex such as a molybdenum-chloranilate complex. The first and second currents can be measured using a working electrode composed of bismuth, gold, carbon or mercury. Measuring the first and second currents using a working electrode can further be performed using a screen printed electrode. Further, the inorganic species added can include silica species. In addition, the first and second currents measured can include voltammetric signals. Measuring the voltammetric signals can be performed using a stripping voltammeter. The voltammetric signals measured using a stripping voltammeter can be measured using a disposable stripping voltammeter.

In another aspect, detecting inorganic species can be performed using a system that includes a detection device and a data processing device. The detection device includes a container designed to at least partially hold a solution in the container. The solution held in the container includes a metal complex. The detection device also includes an electrically conductive member that is at least partially submerged in the solution. The container, the solution and the electrically conductive member are designed to measure a first current corresponding to the metal complex in absences of inorganic species and a second current corresponding to the metal complex in the presence of inorganic species. The data processing device is designed to receive the measured first and second currents from the detection device. The data processing device is also designed to obtain a difference between the first current and the second current, and to identify a concentration of the inorganic species based on the obtained difference.

Implementations can optionally include one or more of the following. The detection device can be designed to measure the first and second currents corresponding to a molybdenum-chloranilate metal complex. Also, the detection device can be designed to measure the second current corresponding to the metal complex in presence of silica species. The electrically conductive member can be composed of one of bismuth, gold, carbon or mercury. In addition, the electrically conductive member can be a screen printed electrode. Further, the detection device can be implemented as a stripping voltammeter. The stripping voltammeter can be a disposable stripping voltammeter. Also, the detection device can be configured to measure the first and second currents by applying an accumulation potential followed by a scanning potential.

In another aspect, a first electrical activity of a electroactive material is detected in absence of a target non-electroactive material. Also, a second electrical activity of the electroactive material is detected in presence of the target non-electroactive material. A difference between the first and second electrical activities is obtained, and based on the obtained difference, a concentration of the target non-electroactive material is identified.

Implementations can optionally include one or more of the following features. Detecting the first and second electrical activities can include applying an accumulation potential followed by a scanning potential. Also, detecting the first and second electrical activities can include detecting the first and second electrical activities of a metal complex in a buffering solution. Further, identifying a concentration of the target non-electroactive material can include identifying a concentration of a target silica species.

In another aspect, a target material that is not electrochemically active is detected by measuring an initial value of an electrochemical property of an electrochemically active medium that is free of the target material. The target material is introduced into the electrochemically active medium. A current value of the electrochemical property of a combination of the target material and the electrochemically active medium a also measured. Based on the current value and the initial value, information on the target material is obtained.

The techniques as disclosed in this specification can be used in ways that provide one or more advantages. For example, an electrochemical detection system can be implemented to use a disposable sensor with inexpensive and simple electronics compared to the typical colorimeter.

Among other things, the subject matter as described in this specification can be implemented as devices, systems, methods of manufacturing the device and/or system, and methods of using the device and/or systems.

BRIEF DESCRIPTION OF THE DRAWINGS

Like reference symbols and designations in the various drawings indicate like elements.

DETAILED DESCRIPTION

Stripping voltammetry can be used as an analytical tool for detecting heavy metal ions in a variety of aqueous samples. Stripping voltammetry can be implemented in various configuration, such as deposition stripping voltammetry, and adsorptive stripping voltammetry. Example techniques, systems and apparatus described in this specification use adsorptive stripping voltammetry. Adsorptive stripping analysis involves formation, adsorptive accumulation and reduction of a surface-active complex of a trace metal (e.g., Molybdenum (Mo)) with a ligand (e.g., chloranilate (CAA)). Thus, adsorptive stripping can be used to measure the concentration of a metal in presence of ligand (e.g., metal complex). An appropriate chelating agent or ligand may be employed. In addition, adsorptive stripping can be used to measure non-electroactive inorganic species by measuring the impact of inorganic species in the presence of heavy metal ions In one aspect, striping voltammetry is used to detect a target material that is not electrochemically active. An initial value of an electrochemical property of an electrochemically active medium that is free of the target material is measured. The target material is introduced into the electrochemically active medium. A current value of the electrochemical property of a combination of the target material and the electrochemically active medium a also measured. Based on the current value and the initial value, information on the target material is obtained.

Figure 1:
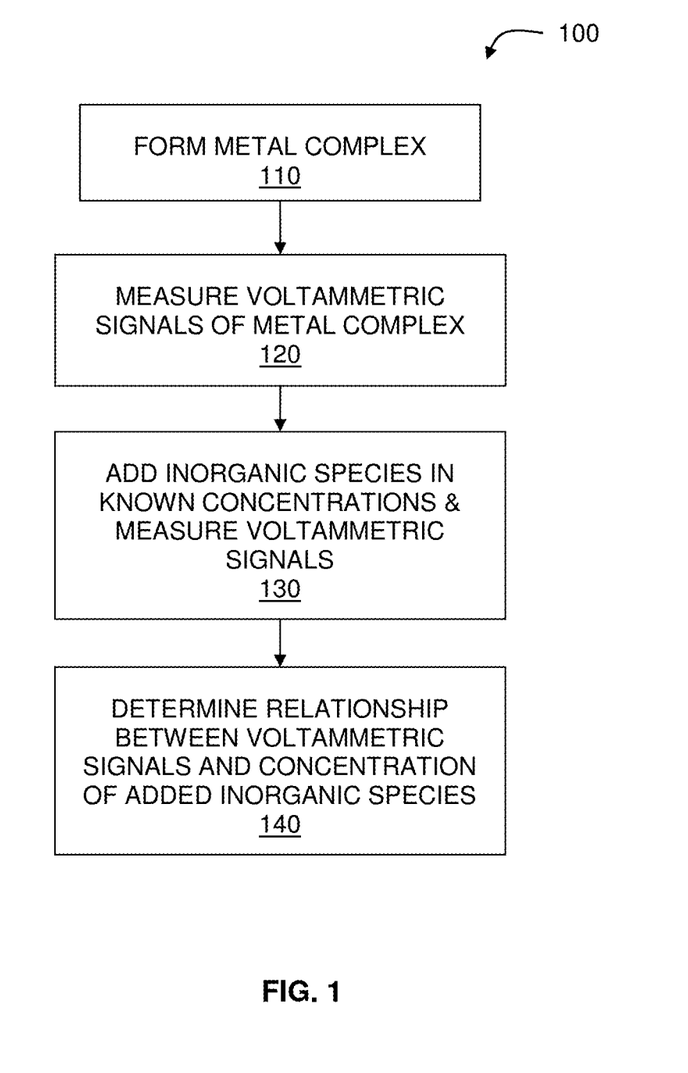
FIG. 1 is a process flow diagram of a process for detecting inorganic species using electrochemical detection.

FIG. 1 is a process flow diagram of an exemplary process 100 for using adsorptive stripping voltammetry to measure inorganic species that are not electroactive. Non-electroactive inorganic species, such as silicic acid, may be detected by measuring the impact of the inorganic species in the presence of electroactive heavy metal ions (e.g., Mo). The process 100 provides a simplified way of determining inorganic species (e.g., silica) indirectly by measuring the effect of the inorganic species on the voltammetric signal associated with an electroactive metal complex.

A metal complex, e.g. molybdenum-chloranilate complex (Mo-CAA), is formed (110) as a reagent. Using absorptive stripping voltammetry (e.g., square wave absorptive stripping voltammetry), the voltammetric signal of the metal complex (e.g., Mo-CAA) is measured (120) in an acetate pH buffer (or other suitable buffering solutions). The voltammetric signal is measured, in this and other implementations, using a working electrode (e.g., bismuth, mercury, gold, etc.) The Molybdenum-chloranilate complex is electroactive and can be detected by voltammetry using a working electrode. An accumulation potential of a predefined amplitude is applied to the metal complex in the buffer for a predetermined period of time, followed by potential scanning with a predefined amplitude, a predefined step potential and a predefined frequency.

Non-electroactive inorganic species (e.g., silica as silicic acid in water) can be detected indirectly using the square wave absorptive stripping voltammetry. A Various concentrations of the non-electroactive inorganic species are added to the metal complex, and voltammetric signals are measured (130) after each addition of a known concentration of the non-electroactive inorganic species. The non-electroactive inorganic species competes with the ligand (e.g., CAA) in binding with the metal. For example, silicic acid competes with chloranilic acid for coordination sites available on the Molybdenum ion, in an acetate pH buffer. Because the Molybdenum-chloranilate complex is electroactive, the metal complex can be detected by voltammetry using a working electrode. The concentration level of Molybdenum-chloranilate complex is held constant, and when a known concentration of the silicic acid is introduced, a reduction in the voltammetric signal is detected. The reductions in the voltammetric signals and the corresponding concentrations of the added non-electroactive inorganic species are compared (140) to obtain a relationship between the signal reduction and the concentration of the added inorganic species.

Figure 2:
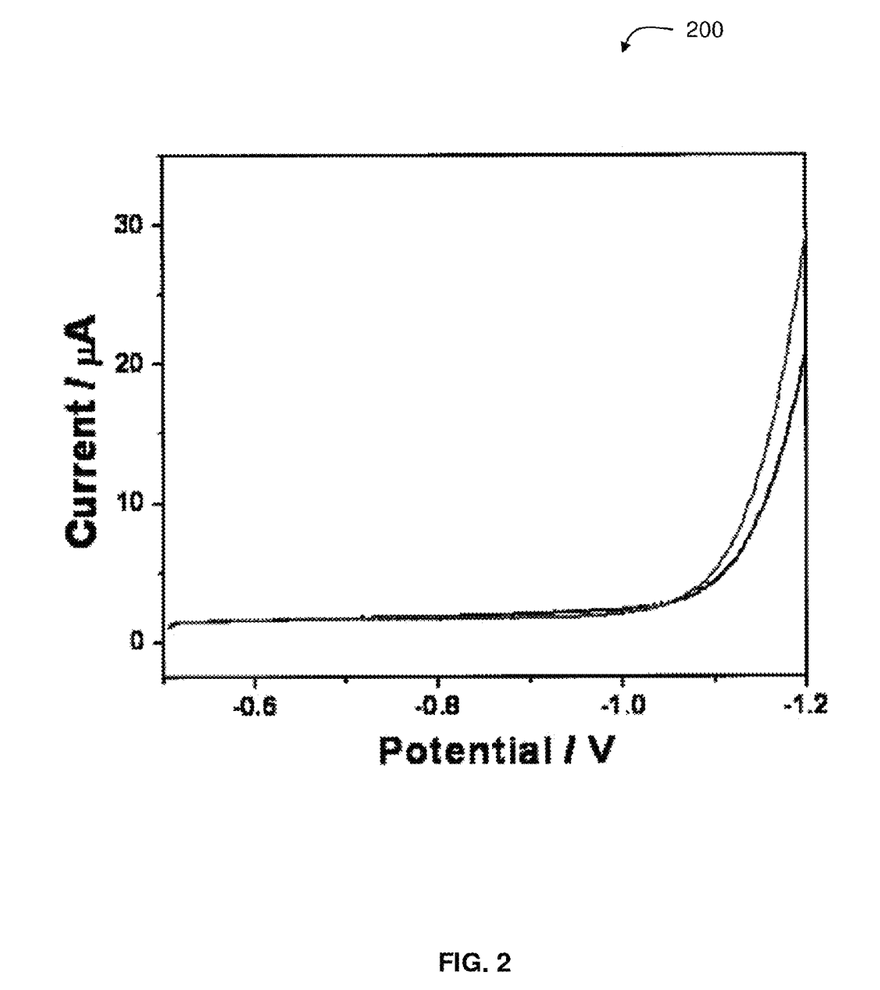
FIG. 2 illustrates voltammetric signals of Mo heavy metal in the absence of ligand.

FIG. 2 shows a voltammetric scan 200 of molybdenum metal ion in an acetate PH buffer. Square-wave adsorptive stripping voltammograms of 50 µg/L Mo with bismuth film electrode (BFE) is shown. In this example, Mo is in a solution of supporting electrolyte, 0.1 M acetate buffer (pH 5.5). An accumulation potential of 0.50V is applied for about 60 seconds with stirring. The accumulation potential is followed by potential scanning with an amplitude of 25 mV, step potential of 4 mV, and a frequency of 25 Hz.

FIG. 2 suggests that, in absence of a ligand (e.g., CAA), the voltammetric signal for Mo alone cannot be determined. Therefore, a metal complex (e.g., Mo-CAA) can be added to detect a voltammetric signal associated with the heavy metal. Adsorptive stripping analysis can enhance the scope of stripping measurements of various trace elements (e.g., Mo). Both voltammetric and potentiometric stripping schemes, with a negative-going potential scan or a constant cathodic current, respectively, can be employed for measuring the adsorbed complex. While adsorptive stripping procedures are typically implemented to show reduction of metal in the adsorbed complex, reduction of ligand can also be shown.

Figure 3:
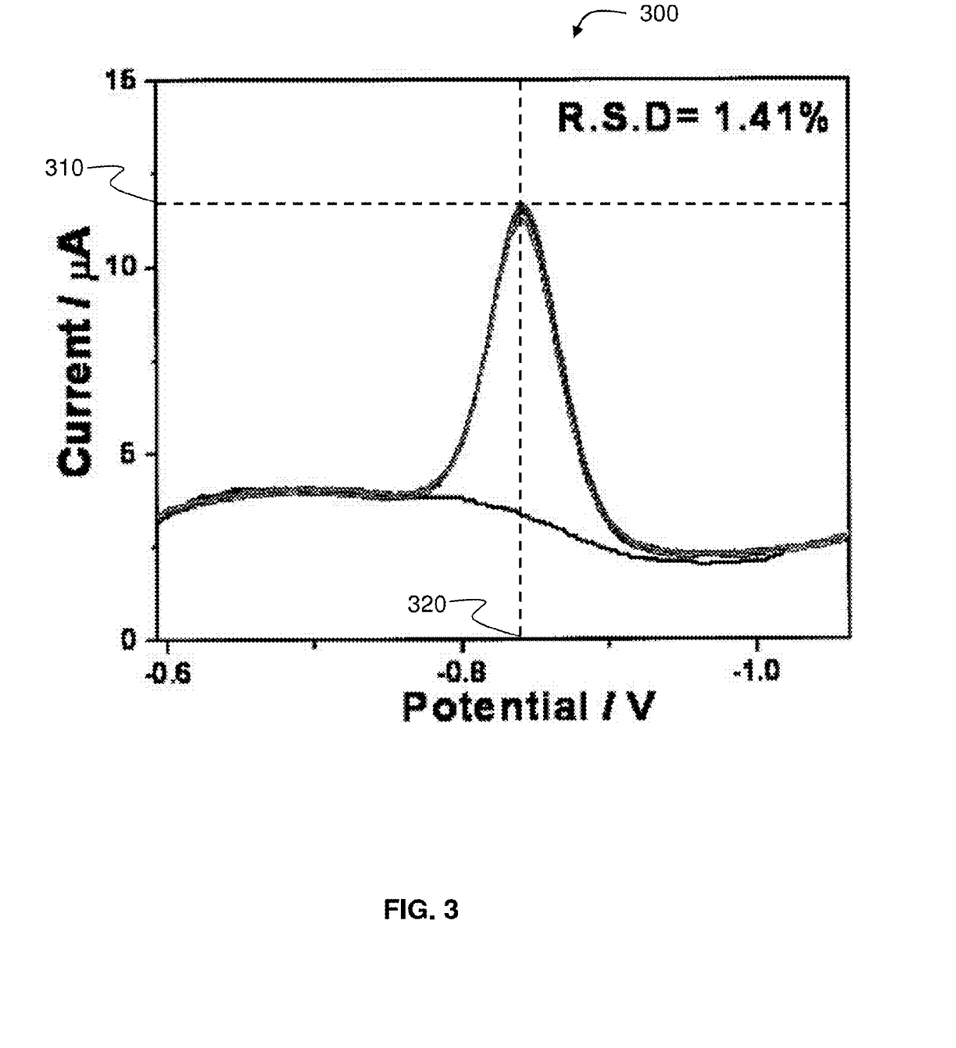
FIG. 3 illustrates voltammetric signals of Mo-CAA complex showing a clear peak current.

FIG. 3 illustrates 10 successive measurements of the molybdenum complex with chloranilic acid, showing good reproducibility. As can be seen when comparing FIGS. 2 and 3, the complex ion is quite evident. Ten successive voltammograms of 50 µg/L Mo in the presence of 50 µM chloranilic acid are shown. Mo was placed in a solution of supporting electrolyte, 0.1 M acetate buffer (pH 5.5). The recording protocol used for these measurements includes an application of an accumulation potential of 0.50V applied for about 60 seconds while stirring, and a potential scanning with an amplitude of 25 mV, a step potential of 4 mV, and a frequency of 25 Hz. The potential scanning may be applied after the accumulation potential. FIG. 3 shows the peak current 310 of the measured voltammetric signal and the potential 320 at which the peak current occurs are measured.

Figure 4:
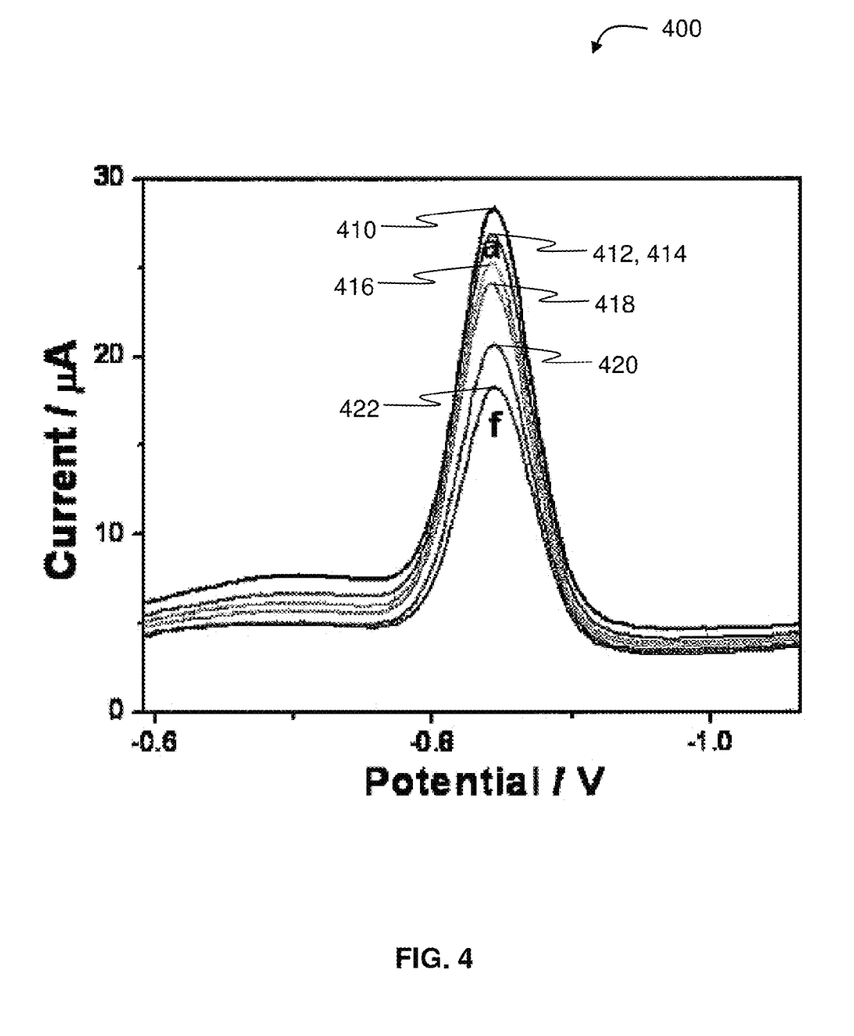
FIG. 4 illustrates voltammetric signals of Mo-CAA complex in the absence and presence of high concentrations of silicic acid.

FIG. 4 illustrates the impact of silicic acid on the voltammetric signal of the molybdenum-chloranilic acid complex under the same operating conditions described in FIGS. 2 and 3. An application of a high level of silicic acid clearly demonstrates the effect of silicic acid on the Mo-CAA complex. A recording protocol used includes square-wave adsorptive stripping voltammograms of 50 μg/L Mo in the presence of 50 μM chloranilic acid. During the measurement, the Mo-CAA complex was placed in a solution of supporting electrolyte, 0.1 M acetate buffer (pH 5.5). Voltammetric signal 410 corresponds to Mo-CAA complex of 50 μg/L Mo in the presence of 50 μM chloranilic acid. Voltammeric signals a-f (412, 414, 416, 418, 420 and 422) show the effects of adding 0.1, 0.5, 1.0, 5.0, 10 and 20 mM silicic acid respectively. The recording protocol further includes application of an accumulation potential of 0.50V applied for about 60 seconds while stirring. The accumulation potential may be followed by a potential scanning with an amplitude of 25 mV, step potential of 4 mV, and a frequency of 25 Hz.

Figure 5:
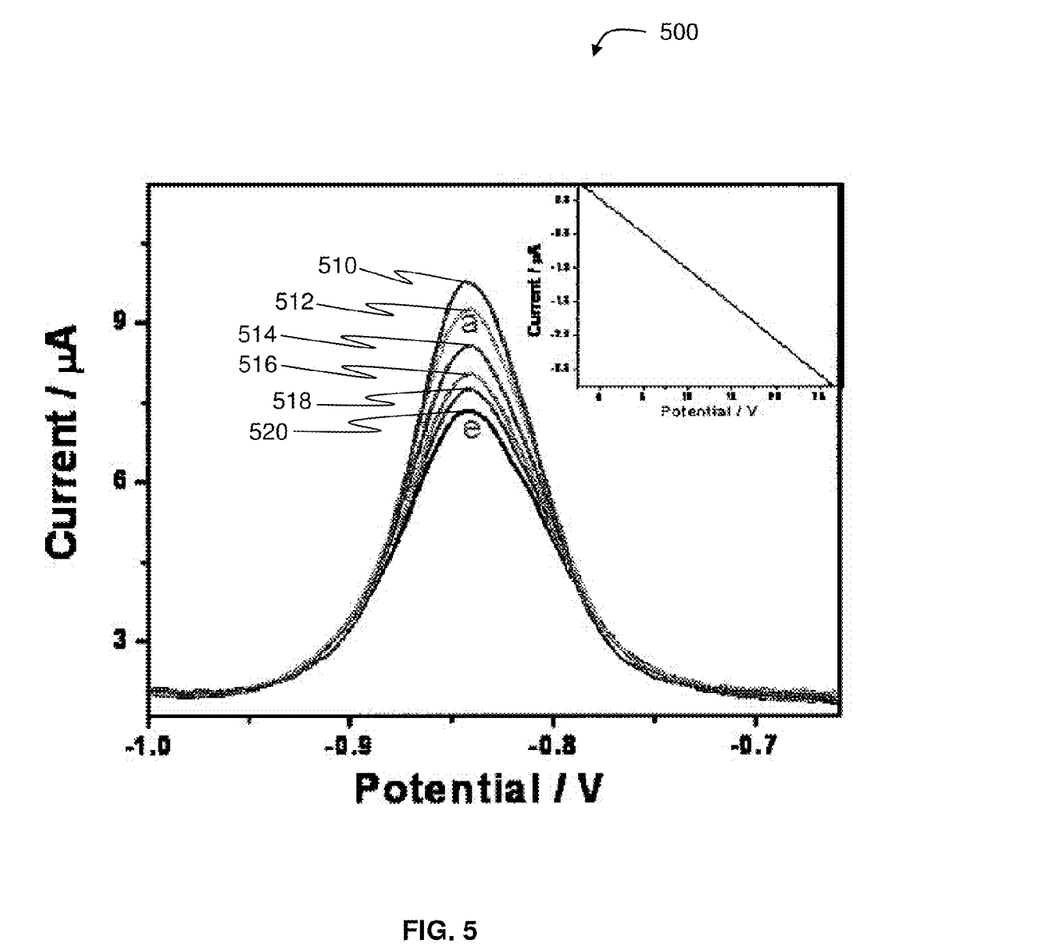
FIG. 5 illustrates voltammetric signals of Mo-CAA complex in the absence and presence of various concentrations of silicic acid in predefined levels.

FIG. 5 illustrates a set of voltammetric signals 500 measured before and after adding known concentrations of silicic acid. The measurement conditions were designed to optimize the detection limit of silicic acid. Square-wave adsorptive stripping voltammograms of 50 μg/L Mo in the presence of 10 μM chloranilic acid was implemented. The Mo-CAA complex was placed in a solution of supporting electrolyte, 0.1 M acetate buffer (pH 5.5). Voltammetric signal 510 corresponds to Mo-CAA complex of 50 μg/L Mo in the presence of 10 μM chloranilic acid. Voltammeric signals a-e (512, 514, 516, 518 and 520) show the effects of adding 5 μM, 10 μM, 15 μM, 20 μM and 25 μM silicic acid respectively. An accumulation potential of 0.50V was applied for 60 seconds with stirring. The accumulation potential was followed by a potential scanning with an amplitude of 25 mV, step potential of 4 mV, and a frequency of 25 Hz.

The amount of chloranilic acid added to the Mo-CAA complex was reduced from 50 μM (refer to FIG. 4) to 10 μM to improve the detection limit of silicic acid under these conditions from 1 μM (refer to FIG. 4) to 5 μM. In these measurements, 5 μM of silicic acid approximately equates to about 300 parts per billion (ppb) of silica. Further improvements in the detection limit are possible by modifying the measurement conditions.

The detection of silica as demonstrated with respect to FIGS. 1 to 5 can be applied to various device form factors and applications where detection of silica or other inorganic species is desired. For example, detection of silica can be used to determine the level of purity of water.

In addition, the systems, apparatus and methods based on what is described in this specification can be used to implement a simple and cost effective electrochemical detection system. For example, a commercial colorimetric instrument can cost US about $1000 or more while an electrochemical detection system as disclosed in this specification may cost less than US $100. The final manufacturing cost for a detection system based on this specification may depend on the user specifications and the desired applications and mode of operation(s).

Figure 6A:
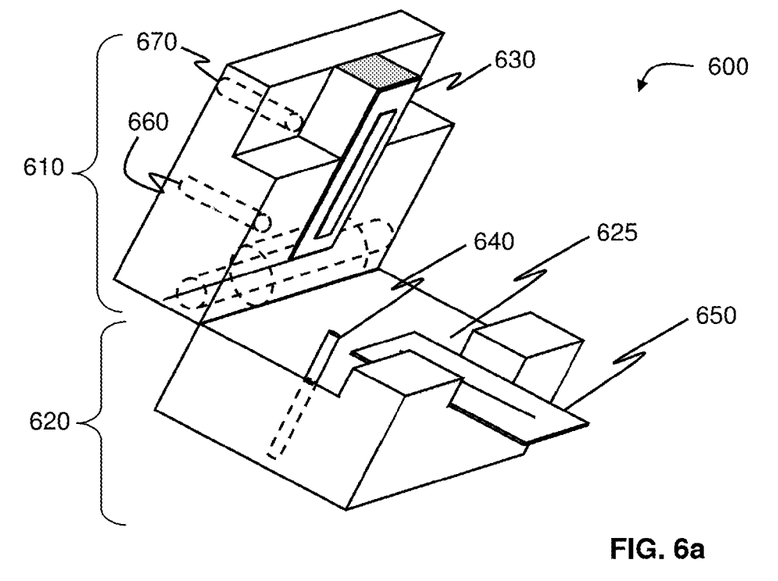
FIG. 6a is a block diagram showing an open configuration of a detection device.

FIG. 6a shows an example of a device 600 for detecting inorganic species such as silica using an analytical process (e.g., adsorptive stripping voltammetry.) The device 600 includes a reference electrode 640, a sensing electrode 650, and a container or a holder 625 for at least partially holding liquid. When the device 600 is implemented as a flow-through device, only a portion of the target liquid is actually held in the container.

The reference electrode 640 is a conductive member that is constructed to at least partially conduct electricity. The reference electrode 640 can be implemented using various conductive materials. For example, a silver wire which provides an electrode (e.g., silver/silver-chloride (Ag/AgCl) when coated with AgCl and immersed in the recording solution) may be used.

The sensing electrode 650 can be implemented using any of a wide variety of carbonaceous electrodes, such as carbon paste electrodes, glassy carbon electrodes, bare carbon electrodes, reticulated carbon electrodes, etc. Other suitable conducting electrodes, e.g., metallic electrodes such as gold, mercury and bismuth electrodes can be used. Further, the sensing electrode 650 can include bismuth coated or plated conducting electrodes and conducting electrodes with bismuth included analyte solution. Bismuth based electrodes provides good conductivity and low toxicity.

The sensing electrode 650 can be coated or plated with a thin film that contains conductive materials (e.g., bismuth). The conductive material-coated sensing electrode 650 can be a carbon fiber or glassy carbon electrode. Alternatively, the sensing electrode 650 can be coated with any conductive material, such as a flat screen-printed carbon electrode. For example, the sensing electrode can be implemented as a disposable screen printed bismuth electrode, which can include an auxiliary electrode, typically platinum.

Other electrode constructions may also be used. Fore example, the electrodes as disclosed in U.S. Pat. Nos. 6,682, 647 and 5,292,423, which are incorporated by reference, can be implemented as the sensing electrode 650. For example, screen-printed electrodes (ExacTech Blood Glucose Strips of Medisense Inc, for example) can be implemented. These strips include working (carbon) and reference electrodes printed on a PVC substrate (with carbon contacts on the opposite side). One printed carbon contact serves as a substrate for the mercury film electrode (since the original working-electrode target area is covered with enzyme/mediator layers). The printed electrode (Ag/AgCl) from another strip serves as reference during the voltammetric experiments. Potentiometric stripping can also be performed using conventional Ag/AgCl electrode of the TraceLab unit. In addition, a platinum wire auxiliary electrode can be used. Further, the sensing electrode 650 can be coated and/or plated with material that includes one or more conductive materials such as bismuth.

Different forms of bismuth can be used to construct the sensing electrode 650. For example, solid bismuth in particulate or granular form can be used. Similarly, bismuth salts can be used as the active electrode material. In some implementations, solid bismuth or bismuth salts are used in a paste, gel or polymeric material which is coated or plated on the sensing electrode 650.

The device 600 can optionally include an inlet port 660 and an outlet port 670. For example, when implemented as a flow through device, a stream of target liquid (e.g., water) can be flowed through the device 600, using the inlet port 660 and outlet port 670. The presence of target inorganic species such as silica in the liquid flowing through the device can be continuously detected. Alternatively, a sample of the target liquid can be deposited into the inlet port 660 to detect silica.

In the open configuration, FIG. 6a also shows a sealing member 630 (e.g., made of rubber or other suitable material) designed to provide a air and/or water tight seal between a first member 610 and the second member 620. The first member includes the inlet port 660, the outlet port 670 and the sealing member 630. The second member 620 includes the reference electrode 640 and the sensing electrode 650.

Figure 6B:
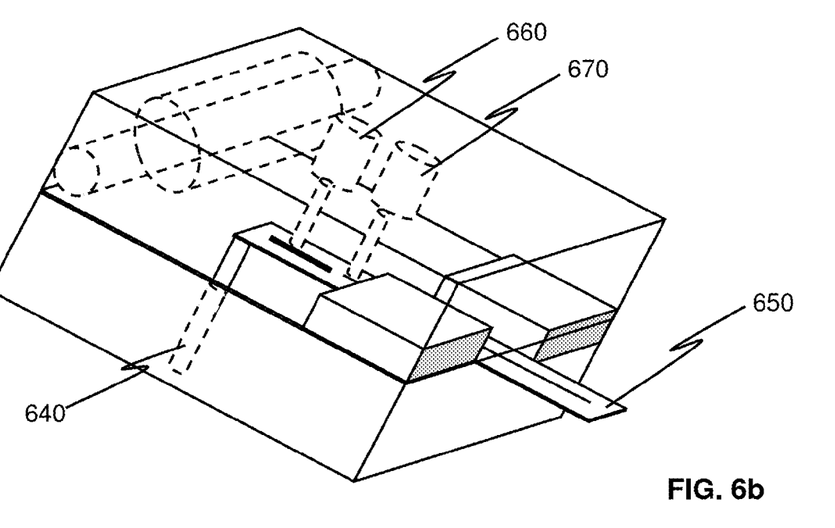
FIG. 6b is a block diagram showing a closed configuration of a detection device.

FIG. 6b is a closed configuration view of an exemplary device 600. When the device 600 is closed and liquid flows through the inlet port 660, an electrical current path is provided across the reference electrode 640 and the sensing electrode.

The form factor of the device 600 can be modified to simplify the analytical process of detecting silica. For example, the device 600 can be designed to simplify sample preparation and accelerate analysis time. The device can be designed to use stripping voltammetry designed to perform in batch mode (e.g., in a beaker) or in a flow through mode. Little or no interaction between the user and the device, other than introducing the sample liquid and/or standards are needed.

Further, the device 600 can be designed to use bismuth-based (or any other conductive material-based) electrodes in a screen printed format for a limited amount of measurements (i.e., disposable). Such disposable device 600 can be manufactured as an inexpensive consumable for a user. For example, the cost of a screen printed electrode can be in the order of 5 US cents per sensor.

Figure 7:
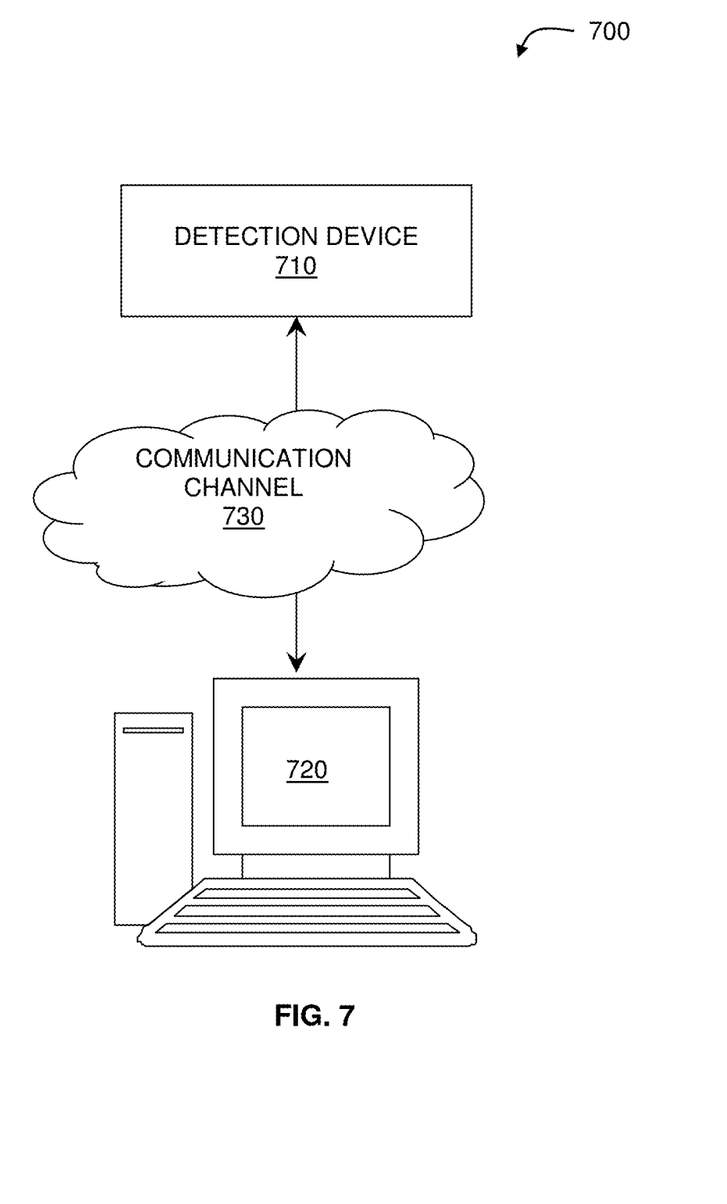
FIG. 7 is a system for detecting inorganic species using electrochemical detection.

FIG. 7 is an exemplary system 700 for detecting inorganic species such as silica using electrochemical detection. The system 700 includes a detection device 710 (e.g., implemented in a dedicated flow cell design) coupled to a data processing device 720. The detection device 710 can be substantially as described with respect to FIG. 6. Alternatively, the detection device 710 can be implemented using other form factors.

The data processing device 720 can be implemented as one of various electronics for receiving data from the detection device 710 and processing the received data. For example, the data processing device 720 can be implemented as a personal computer, a server computer, a portable computing device, etc. In addition, the data processing device 720 can include various components such as a central processing unit (CPU) designed to execute software programs, such as a program (not shown) that perform data acquisition and analyses of the data received from the detection device 710.

For example, the program can communicate an appropriate recording protocol for stripping voltammetry (e.g., the accumulation potential and the potential scanning with an amplitude, step potential, and a frequency as described with respect to FIGS. 1-5.) Also, the program can be designed to compare the received voltammetric signals with the concentrations of the added silica to determine the effects of different concentrations of silica on the voltammetric signals. The determined effects are used to determine an unknown concentration of silica in water, for example by measuring the reduction in voltammetric signals.

The data processing device 720 receives the data from the detection device 710 through a bidirectional communication channel 730. The bidirectional communication channel 730 can include any one of wired or wireless connections. Wired connections can be compatible with Universal Serial Bus connections, FireWire connections, parallel connections, etc. Wireless connections can be compatible with Bluetooth, WiFi, Wimax, etc. In some implementations, the detection device can be placed at a remote location (e.g., in the field, such as a body of water) for testing a water source at the remote location. The data collected using the detection device 710 is transmitted to the data processing device 720 over a network such as wide area network (WAN), local area network (LAN), or the internet. In some implementations, the system 700 can be implemented as a stand alone system or as a part of a larger system such as network system.

Figure 8:
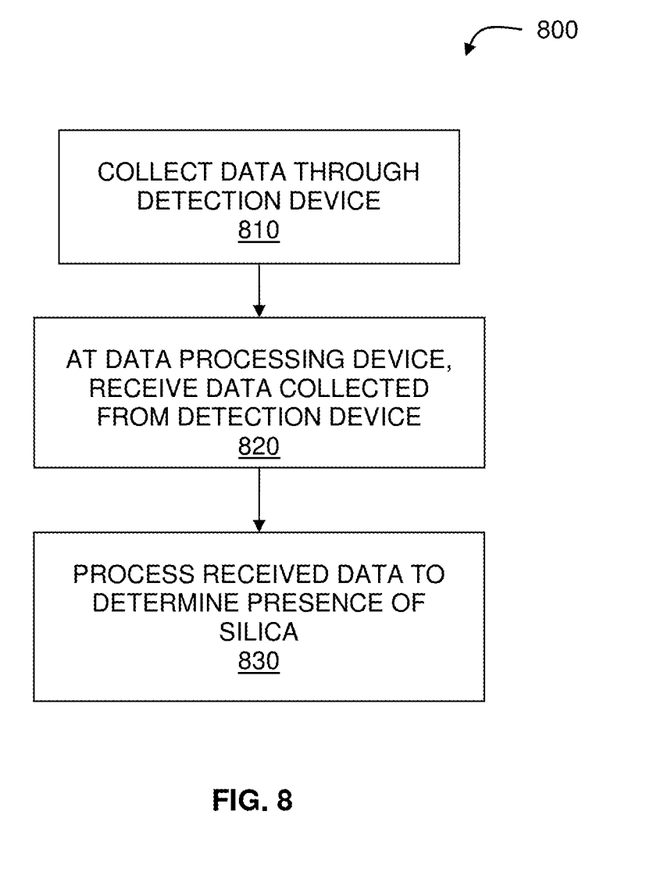
FIG. 8 is a process flow diagram of a process for using an electrochemical detection system.

FIG. 8 is an exemplary process flow diagram of a process 800 for operating the system 700 for detecting inorganic species such as silica. At 810, using adsorptive stripping voltammetry, data (e.g., voltammetric signals of a metal complex) is collected through the detection device 710. At 820, the data processing device 720 receives the collected data. At 830, the received data is processed to determine the presence of silica and its concentration.

In some implementations, the system 700 is implemented as a specific detection system that uses square ware absorptive stripping voltammetry. The detection system can use a bismuth electrode to measure the competition of silicic acid and chloranilic acid for the molybdenum metal ion. The system 700 can be developed as a suitable and inexpensive system for electrochemical detection of silica indirectly by measuring heavy metal ions in pure and ultrapure water in the presence of the silica ligand.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus. The tangible program carrier can be a propagated signal or a computer readable medium. The propagated signal is an artificially generated signal, e.g., a machine-generated electrical, optical, or electromagnetic signal, that is generated to encode information for transmission to suitable receiver apparatus for execution by a computer. The computer readable medium can be a machine-readable storage device, a machine-readable storage substrate, a memory device, a composition of matter effecting a machine-readable propagated signal, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, or declarative or procedural languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, input from the user can be received in any form, including acoustic, speech, or tactile input.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results.

Only a few implementations and examples are described and other implementations, enhancements and variations can be made based on what is described and illustrated in this application. For example, implementations are not limited to Mo-CAA complex, and other heavy metals and ligands are possible. Also, the recording protocol for adsorptive stripping voltammetry can be varied (e.g., amplitude of the accumulation potential of 0.50V; duration of accumulation potential applied; stirring or not stirring; amplitude of potential scanning; an amplitude of the step potential; a frequency of the potentials applied; etc.)

What is claimed is:

1. A method comprising:
   applying a voltage to a buffering solution, which comprises a molybdenum-chloranilate complex and is free of inorganic silica species;
   measuring a first current associated with the molybdenum-chloranilate complex in absence of the inorganic silica species;
   adding the inorganic silica species into the buffering solution;
   measuring a second current associated with the molybdenum-chloranilate complex in the presence of the added inorganic silica species; and
   obtaining a difference between the first current and the second current to identify a concentration of the added inorganic silica species in the buffering solution,
   wherein measuring the first and second currents comprises using a working electrode comprising bismuth.

2. The method of claim 1, wherein measuring the first and second currents comprises applying an accumulation potential followed by a scanning potential.

3. The method of claim 2, wherein the applying an accumulation potential comprises applying an accumulation potential of an amplitude comprising 0.5 volts.

4. The method of claim 2, wherein the applying an accumulation potential comprises applying an accumulation potential for a time period that includes 60 seconds.

5. The method of claim 2, wherein applying a scanning potential comprises applying a scanning potential having at least one of a 25 millivolt amplitude, a step potential of 4 millivolt, and a frequency of 25 hertz.

6. The method of claim 1, wherein measuring the first and second currents comprises using a working electrode comprising a carbon-based electrode having a bismuth coating.

7. The method of claim 6, wherein measuring the first and second currents using a working electrode comprises using a screen printed bismuth electrode.

8. The method of claim 1, wherein measuring the first and second currents comprises measuring voltammetric signals.

9. The method of claim 8, wherein measuring the voltammetric signals comprises using a stripping voltammeter.

10. The method of claim 9, wherein measuring the voltammetric signals using a stripping voltammeter comprises using a disposable stripping voltammeter.

11. An apparatus for measuring non-electroactive materials in liquids, the apparatus comprising:
   A. a detection device comprising
      i. a container configured to at least partially hold a buffering solution in the container, the buffering solution comprising a molybdenum-chloranilate complex; and
      ii. an electrically conductive member comprising bismuth at least partially submerged in the buffering solution, wherein the container, the buffering solution and the electrically conductive member are configured to measure a first current corresponding to the molybdenum-chloranilate complex in the absence of an inorganic silica species and a second current corresponding to the molybdenum-chloranilate complex in the presence of the inorganic silica species; and
   B. a data processing device configured to receive the measured first and second currents from the detection device and to obtain a difference between the first current and the second current to identify a concentration of the inorganic silica species.

12. The apparatus of claim 11, wherein the electrically conductive member comprises a carbon-based electrode having a bismuth coating.

13. The apparatus of claim 11, wherein the electrically conductive member comprises a screen printed bismuth electrode.

14. The apparatus of claim 11, wherein the detection device is configured as a stripping voltammeter.

15. The apparatus of claim 14, wherein the stripping voltammeter comprises a disposable stripping voltammeter.

16. The apparatus of claim 11, wherein the detection device is configured to measure the first and second currents by applying an accumulation potential followed by a scanning potential.

17. An apparatus for measuring inorganic silica species in a liquid stream or sample using electrochemical detection, the apparatus comprising:
   a flow-through detection device configured to continuously detect an inorganic silica species in a liquid stream or sample; and
   a data processing device,
   wherein the flow-through detection device comprises:
      i. a container having an inlet port and an outlet port, the inlet port configured to receive a liquid stream or sample comprising a buffering solution and a molybdenum-chloranilate complex that will flow through the device; and
      ii. a bismuth-based electrode at least partially submerged in the buffering solution, wherein the container, the buffering solution, and the bismuth-based electrode are configured to measure a first current corresponding to the molybdenum-chloranilate complex in the absence of an inorganic silica species and a second current corresponding to the molybdenum-chloranilate complex in the presence of the inorganic silica species, and
   wherein the data processing device is configured to receive the measured first and second currents from the detection device and to obtain a difference between the first current and the second current to identify a concentration of the inorganic silica species.

18. The apparatus of claim 17, wherein the bismuth-based electrode is a carbon electrode having a bismuth coating.

19. The apparatus of claim 17, wherein the bismuth-based electrode is a disposable screen printed bismuth electrode.

* * * * *